(12) United States Patent
Fonte

(10) Patent No.: US 8,774,921 B2
(45) Date of Patent: *Jul. 8, 2014

(54) ELECTROMAGNETIC INTERFERENCE SHIELDING IN AN IMPLANTABLE MEDICAL DEVICE

(71) Applicant: Cameron Health, Inc., San Clemente, CA (US)

(72) Inventor: Timothy A. Fonte, San Clemente, CA (US)

(73) Assignee: Cameron Health, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/945,343

(22) Filed: Jul. 18, 2013

(65) Prior Publication Data

US 2013/0304148 A1   Nov. 14, 2013

Related U.S. Application Data

(60) Division of application No. 13/572,451, filed on Aug. 10, 2010, now Pat. No. 8,538,531, which is a division of application No. 12/846,212, filed on Jul. 29, 2010, now Pat. No. 8,244,356, which is a continuation of application No. 11/883,987, filed on Aug. 4, 2007, now Pat. No. 7,769,457.

(51) Int. Cl.
    *A61N 1/375* (2006.01)

(52) U.S. Cl.
    USPC ............................................................ 607/36

(58) Field of Classification Search
    CPC ........................................................ A61N 1/375
    USPC ............................................................ 607/36
    See application file for complete search history.

(56) References Cited

U.S. PATENT DOCUMENTS

| | | |
|---|---|---|
| 4,441,498 A | 4/1984 | Nordling |
| 5,456,698 A | 10/1995 | Byland et al. |
| 5,660,892 A | 8/1997 | Robbins et al. |
| 5,749,910 A | 5/1998 | Brumwell et al. |
| 5,814,090 A * | 9/1998 | Latterell et al. ............... 607/36 |
| 6,631,555 B1 | 10/2003 | Youker et al. |
| 6,647,292 B1 | 11/2003 | Bardy et al. |
| 6,721,597 B1 | 4/2004 | Bardy et al. |
| 6,721,602 B2 | 4/2004 | Engmark et al. |
| 7,769,457 B2 * | 8/2010 | Fonte ............................. 607/36 |

(Continued)

FOREIGN PATENT DOCUMENTS

| EP | 1704894 A2 | 9/2006 |
|---|---|---|
| EP | 1704894 A3 | 2/2007 |

OTHER PUBLICATIONS

"U.S. Appl. No. 12/846,212, Non Final Office Action mailed Dec. 6, 2011", 7 pgs.

(Continued)

*Primary Examiner* — Eric D. Bertram
(74) *Attorney, Agent, or Firm* — Schwegman, Lundberg & Woessner, P.A.

(57) ABSTRACT

EMI shields for use in implantable medical devices that include inner and outer metal layers separated by a dielectric layer. When assembled as medical devices, the outer metal layer of an illustrative EMI shield is placed into electrical contact with a conductive inner surface of an associated canister for an implantable medical device.

13 Claims, 27 Drawing Sheets

(56) References Cited

U.S. PATENT DOCUMENTS

| | | |
|---|---|---|
| 8,244,356 B2 | 8/2012 | Fonte |
| 8,538,531 B2 | 9/2013 | Fonte |
| 2004/0045158 A1 | 3/2004 | Youker et al. |
| 2006/0217792 A1 | 9/2006 | Hussein et al. |
| 2007/0106332 A1 | 5/2007 | Denker et al. |
| 2012/0310294 A1 | 12/2012 | Fonte |

OTHER PUBLICATIONS

"U.S. Appl. No. 12/846,212, Response filed Jan. 27, 2012 to Non Final Office Action mailed Dec. 6, 2011", 4 pgs.

"U.S. Appl. No. 12/846,212, Response filed Nov. 21, 2011 to Restriction Requirement mailed Oct. 24, 2011", 5 pgs.

"U.S. Appl. No. 13/572,451, Non Final Office Action mailed Feb. 27, 2013", 7 pgs.

"U.S. Appl. No. 13/572,451, Response filed Feb. 3, 2013 to Restriction Requirement mailed Jan. 29, 2013", 6 pgs.

"U.S. Appl. No. 13/572,451, Response filed Apr. 1, 2013 to Non Final Office Action mailed Feb. 27, 2013", 7 pgs.

"European Application Serial No. 08827070.7, Office Action mailed Apr. 21, 2010", 10 pgs.

"European Application Serial No. 08827070.7, Response filed May 28, 2010 to Office Action mailed Apr. 21, 2010", 9 pgs.

"International Application Serial No. PCT/US2008/071972, International Search Report mailed Nov. 13, 2008", 3 pgs.

"International Application Serial No. PCT/US2008/071972, Written Opinion mailed Nov. 13, 2008", 7 pgs.

\* cited by examiner

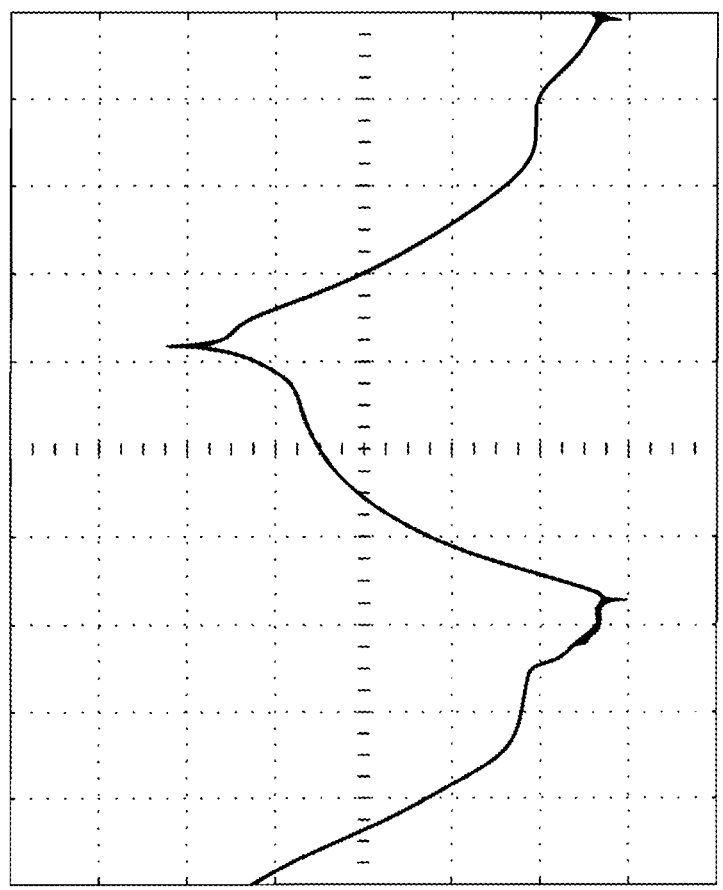

ELECTROMAGNETIC INTERFERENCE SHIELDING IN AN IMPLANTABLE MEDICAL DEVICE

RELATED APPLICATIONS

This application is a divisional of U.S. patent application Ser. No. 13/572,451, filed Aug. 10, 2012, now U.S. Pat. No. 8,538,531, which is a divisional of U.S. patent application Ser. No. 12/846,212, filed Jul. 29, 2010, published as U.S. 2010-0305654, now U.S. Pat. No. 8,244,356, and titled ELECTROMAGNETIC INTERFERENCE SHIELDING IN AN IMPLANTABLE MEDICAL DEVICE, which is a continuation of U.S. patent application Ser. No. 11/833,987, filed Aug. 4, 2007, now U.S. Pat. No. 7,769,457, and titled ELECTROMAGNETIC INTERFERENCE SHIELDING IN AN IMPLANTABLE MEDICAL DEVICE, the entire disclosures of which are incorporated herein by reference.

FIELD

The present invention relates to the field of implantable medical devices. More particularly, the present invention relates to implantable medical devices that include internal shielding to prevent electromagnetic interference with circuitry contained in such devices.

BACKGROUND

Implantable cardiac stimulus devices, as well as many other implantable medical devices, typically include control circuitry that is adapted to perform various functions such as sensing, communication and/or stimulus delivery. Such devices operate within a patient's body, and are subject to various sources of electromagnetic interference (EMI) including, for example, noise from other electrical devices inside or outside of the patient's body, power line noise, noise generated by the patient's body itself, and, for some devices, noise that the device itself generates. For example, implantable cardiac stimulus devices typically deliver electric pulses to regulate or correct cardiac activity, and their sensing algorithms are often configured to avoid capturing self-generated signals. Some such devices, known as implantable cardioverter defibrillators (ICDs), deliver very large stimuli to shock a patient's heart out of an arrhythmic state such as ventricular tachycardia or ventricular fibrillation. When large pulses are delivered, it is desirable to limit the effects of the large pulse on operation of internal circuitry. New and alternative designs for limiting such effects in implantable medical devices are desired.

SUMMARY

The present invention, in an illustrative embodiment, includes an implantable medical device that includes operational circuitry contained in a housing. An EMI shield is disposed between the operational circuitry and the housing. The EMI shield, in an illustrative embodiment, includes an inner conductive layer which is coupled to a reference voltage. The EMI shield also includes an outer conductive layer that is exposed on its outer surface to the interior of the housing. The inner and outer conductive layers, which may be formed of conductive metals, for example, silver or copper, are separated by a dielectric layer. By exposing the outer conductive layer to contact with the interior of the housing, air gaps between the outer conductive layer and the housing are prevented from becoming sources for nonlinear electrical conduction such as corona discharge.

BRIEF DESCRIPTION OF THE DRAWINGS

FIG. 8B shows an oscilloscope output illustrating corona discharges when the design of FIGS. 2A-2B is used as an EMI shield inside the varnished canister of FIG. 8A during a simulated high voltage signal application;

DETAILED DESCRIPTION

The following detailed description should be read with reference to the drawings. The drawings, which are not necessarily to scale, depict illustrative embodiments and are not intended to limit the scope of the invention.

Figure 1A:
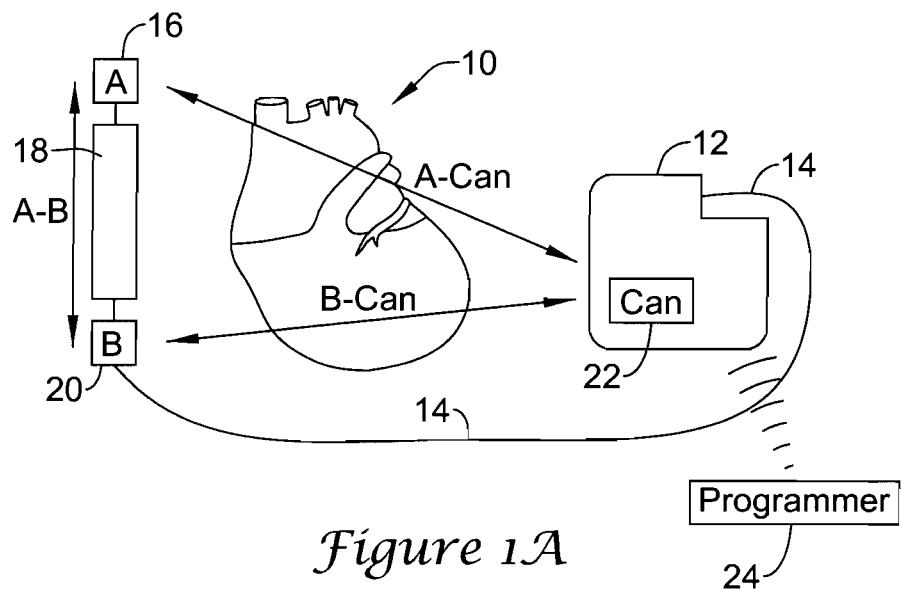
FIGS. 1A-1B show respective subcutaneous and transvenous cardiac stimulus systems.
Figure 1B:
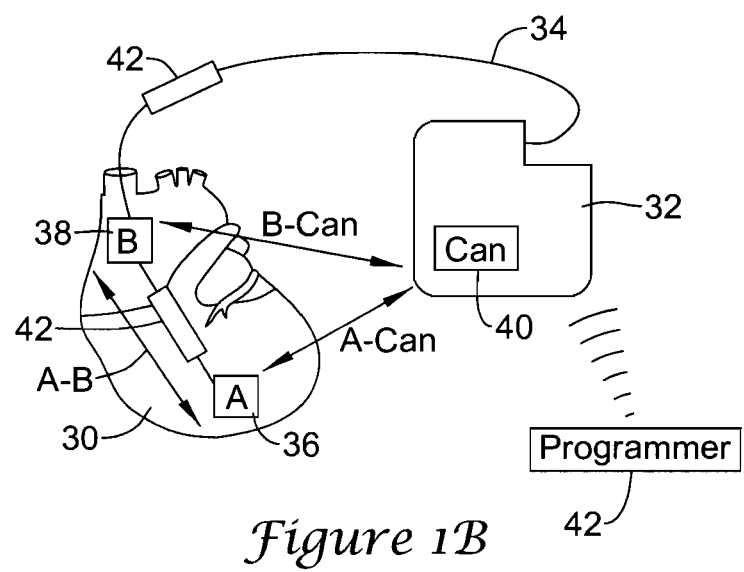

FIGS. 1A-1B, respectively, show subcutaneous and transvenous implanted cardiac stimulus systems relative to the heart. Referring to FIG. 1A, the patient's heart 10 is shown in relation to an implanted, subcutaneous cardiac stimulus system including a canister 12. A lead 14 is secured to the canister and includes sensing electrode A 16, coil electrode 18, and sensing electrode B 20. A can electrode 22 is shown on the canister 12. Illustrative subcutaneous systems are shown in U.S. Pat. Nos. 6,647,292 and 6,721,597, and the disclosures of these patents are incorporated herein by reference. Some embodiments include a unitary system having two or more electrodes on a housing as set forth in the '292 patent, rather than that which is shown in FIG. 1A. A unitary system including an additional lead may also be used.

Referring now to FIG. 1B, a transvenous system is shown relative to a patient's heart 30. The transvenous cardiac stimulus system includes a canister 32 connected to a lead 34. The lead 34 enters the patient's heart and includes electrodes A 36 and B 38. Additional electrodes for sensing or stimulus delivery may also be included, and also may be used for sensing in some embodiments of the present invention. In the illustrative example, electrode A 36 is located generally in the patient's ventricle, and electrode B 38 is located generally in the patient's atrium. The lead 34 may be anchored into the patient's myocardium. The lead 34 may also include one or more coil electrodes, either interior to or exterior to the heart, as shown at 42, which may be used to deliver stimulus and/or to sense cardiac or other activity, such as respiration. A can electrode 40 is shown on the canister 32. With this system, plural sensing vectors may be defined as well, in first and second polarities. In both FIGS. 1A and 1B, one or more sensing electrodes may also be used for stimulus delivery. Some embodiments of the present invention may be used in combination systems that may include sensing vectors defined between two subcutaneous electrodes, a subcutaneous electrode and a transvenous electrode, or two transvenous electrodes.

The systems shown in FIGS. 1A-1B may include operational circuitry and a power source housed within the respective canisters. The power source may be, for example, a battery or bank of batteries. The operational circuitry may be configured to include such controllers, microcontrollers, logic devices, memory, and the like, as selected, needed, or desired for performing the illustrative methods set forth herein. The operational circuitry may (although not necessarily) further include a charging sub-circuit and a power storage sub-circuit (for example, a block of capacitors) for building up a stored voltage for cardiac stimulus taking the form of cardioversion and/or defibrillation pulses or stimuli. The operational circuitry may also be adapted to provide a pacing output. Both cardioversion/defibrillation and pacing sub-circuitry and capacities may be incorporated into a single device. Methods of signal analysis may be embodied in hardware within the operational circuitry and/or as instruction sets for operating the operational circuitry and/or in the form of machine-readable media (optical, electrical, magnetic, etc.) embodying such instructions and instruction sets.

In illustrative examples, a cardioversion/defibrillation pulse may be supplied by a transvenous ICD in a variety of amplitudes, energy levels, and formats. Biphasic and monophasic waveforms can be used. Constant voltage or constant current formats may be used, though it is typical to provide an output that is "tilted," that is, output voltage decays from an initial value over time as the energy storage circuit of the ICD discharges. Tilt is measured in terms of final voltage relative to initial voltage. For example, an existing line of Medtronic® transvenous devices (GEM® II VR) can be programmed to deliver initial output voltages of 83-736 volts with 0.4 to 30 Joules of delivered energy in a biphasic waveform with 50% tilt (assuming delivery into 75 ohms of resistance). Depending upon electrode placement and energy delivery, voltages as low as 50 volts may be useful in some ICDs. Subcutaneous ICDs are being developed and are expected to utilize voltage outputs that will include at least the upper portions of the delivery energy and voltage ranges for transvenous devices, while also using higher delivery energies and voltages when necessary. For example, delivery voltages in the range of 1350 volts, with energy in the range of 30-40 Joules, and up to 80 Joules, or more, are expected to be within the range of such devices, although higher and lower values may be realized. Electrode positioning can play a role in modifying such ranges. These values are merely illustrative and should not be taken as limiting.

Each of the devices 12, 32 may further include such components as would be appropriate for communication (such as RF communication or inductive telemetry) with an external device such as a programmer. To this end, programmers 24 (FIG. 1A) and 42 (FIG. 1B) are also shown. For example, during an implantation procedure, once the implantable device 12, 32 and leads (if included) are placed, the programmer 24, 42 may be used to activate and/or direct and/or observe diagnostic or operational tests. After implantation, the programmer 24, 42 may be used to non-invasively determine the status and history of the implanted device. The programmer 24, 42 and the implanted device 12, 32 are adapted for wireless communication allowing interrogation of the implanted device. The programmers 24, 42 in combination with the implanted devices 12, 32 may also allow annunciation of statistics, errors, history and potential problem(s) to the user/physician. The particulars of operational circuitry, signal analysis, lead placement, implantation, communication and programmers may vary widely in embodiments associated with the present invention.

Figure 2A:
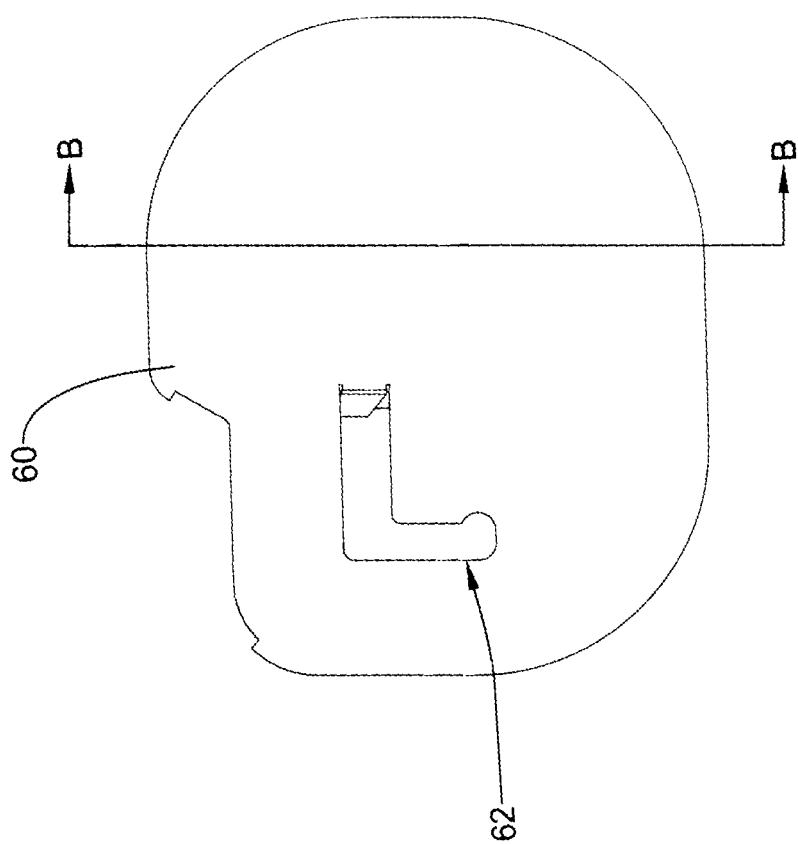
FIGS. 2A-2B show perspective and cross-sectional views of an EMI shield.
Figure 2B:
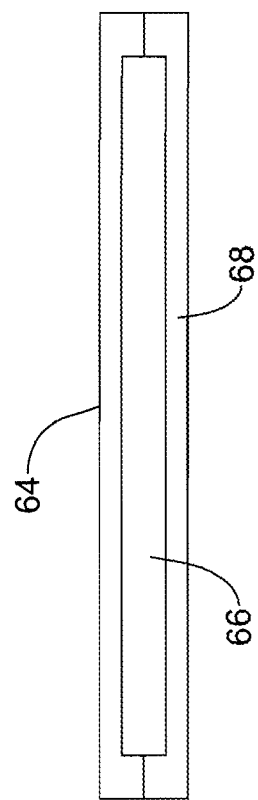

FIGS. 2A-2B show a perspective and a cross-sectional view of an EMI shield. The shield 60 includes a solder pad 62 that allows soldering of a layer of the EMI shield to the ground plane of the associated circuitry. During assembly, a relatively small patch-type pad may be placed over the solder pad 62 to electrically isolate it from an associated canister.

As shown by FIG. 2B, a cross section of the EMI shield shows an outer dielectric layer 64, which covers a metal layer 66, which is placed on an inner dielectric layer 68. In an illustrative example, the dielectric layers 64, 68 include 1 mil of polyimide. At the edges of the shield, the metallic layer 66 may be pulled back to reduce edge effects. Any conductive metal or alloy maybe used as metallic layer 66; in illustrative examples, copper and/or silver are used. In an illustrative example, the metallic layer 66 was pulled back 10 mils from the edge of the EMI shield 60. Further, in the illustrative example, the solder pad 62 was used to tie the metallic layer 66 to a reference voltage (i.e., ground) for the overall device. Certain shortcomings of this design are explained in further detail below. The EMI shield 60 is used by placing it between housed operational circuitry and a canister provided to house the operational circuitry, as shown by FIG. 3.

Figure 3:
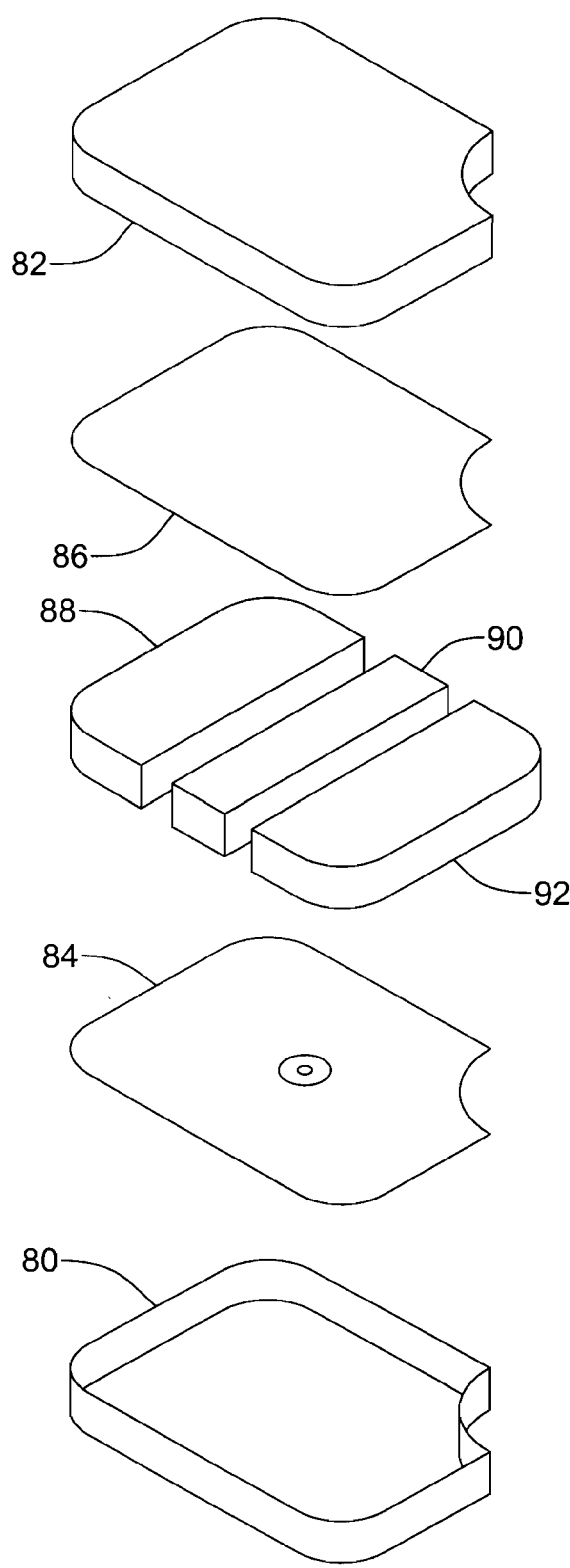
FIG. 3 is an exploded view of an implantable medical device illustrating the assembly of a canister, EMI shields, and operational circuitry including batteries and capacitors.

FIG. 3 is an exploded view of an implantable medical device illustrating the assembly of a canister, EMI shields, and operational circuitry including batteries and capacitors. The canister includes a first component 80 and a second component 82. The first and second components 80, 82 may be made of any suitable biocompatible material. Titanium is an illustrative material, although other materials may be used in place of or in combination with titanium. Portions of the outside of the first and second components 80, 82 may be coated, shaped, or treated in any suitable fashion. In some embodiments, the first and second components may be configured to matingly fit together, for example, in a snap fit or an overlapping fit. Typically, the completed device will have a weld seam joining the first component 80 to the second component 82, although additional intermediate members may also be included on the inside or outside of the device, and welding need not be used for some embodiments using, for example, adhesive or snap-fit.

Internal parts shown in the exploded view include a first EMI shield portion 84 and a second EMI shield portion 86. A solder pad is shown on the first EMI shield portion 84. Sandwiched between the EMI shield portions 84, 86 is the operational circuitry of the device. In the illustrative embodiment shown, the operational circuitry is shown in a highly simplified fashion, and includes a capacitor block 88, control components 90, and a battery 92. The operational circuitry shown is likely for such devices as ICDs or other devices that provide electrical stimuli to a patient. The precise details of the control components and/or the operational circuitry generally may vary widely depending upon the desired functionality of the device.

Generally, the operational circuitry will define a ground potential for operation of its circuitry. A reference output, which may be the operational circuitry ground or some other voltage defined relative to the operational circuitry ground, may be electrically connected to the metal layer of an associated EMI shield at the solder pad. A frame (not shown) may be included to hold the operational circuitry parts 88, 90, 92, in place.

While much of the present description is directed toward implantable cardiac stimulus devices, particularly ICDs, it should be understood that the concepts, devices and methods disclosed herein for providing EMI shielding in an implantable medical device can be applied more broadly in the field of implantable medical devices. This may include other implantable devices that house electronics and are susceptible to noise interference.

A number of the Figures that follow show oscilloscope outputs that were generated during actual testing of devices during simulated high voltage pulse delivery. The testing methods can be understood by viewing the exploded view of FIG. 3. The illustrative tests referred to in the Figures which follow were performed by providing one of the EMI shield portions 84, 86 against a corresponding canister component 80, 82. Substitutes for the relatively expensive operational circuitry components that would be used in an actual device were provided, including a non-functional battery, capacitors and an associated frame that would be used in an actual device to hold the operational circuitry together in place within the canister. Weights were placed on these "substitutes" to hold everything in place, but the second side of the canister was not attached, such that the internal components, particularly the EMI shield portion 84, 86 remained accessible. In testing, a voltage was applied between a sandwiched metal layer of the shield portion 84, 86 and the metallic canister component 80, 82. Resultant currents were then observed. This simulates application of a stimulus pulse by the use of an electrode disposed on the canister in combination with an electrode disposed on a lead. These methods were used in generating the following figures, with the exception of FIGS. 15A-15B and 16A-16B, which provide information captured using different testing conditions.

For FIGS. 6B, 7B, 8B, 9, 12, 13A-13B and 14A-14B, testing was performed using a 60-Hz output. The oscilloscope views in these Figures were captured with an applied signal of 1000 Vrms. Nonlinearities caused by corona discharge show up as spikes on the oscilloscope outputs. Actual measurement of the amount of current caused by the corona discharge was calculated by monitoring the voltage across a series 10 kilohm resistor. This form of simulation of high voltage pulse delivery is believed to provide a reasonable and useful understanding of whether and how well the proposed EMI shields performed with respect to corona discharge.

Figure 4A:
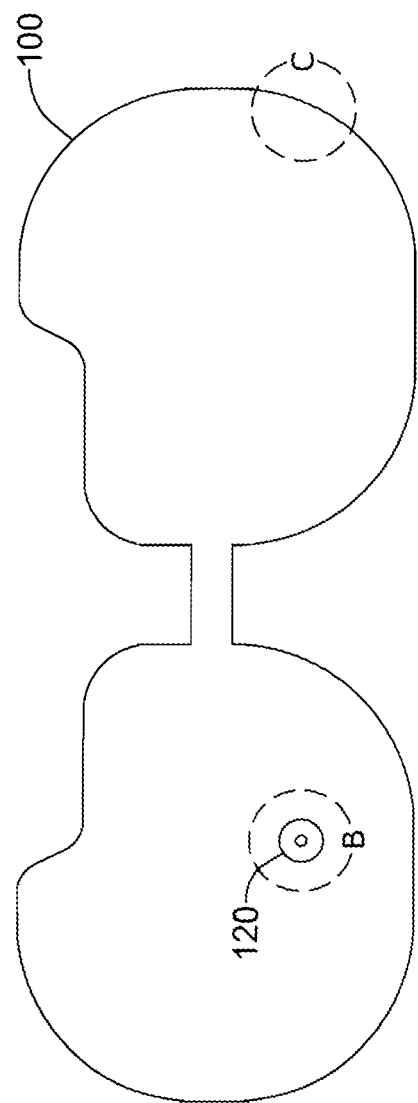
FIGS. 4A-4C illustrate, in plan and partial sectional views, an embodiment of an EMI shield.
Figure 4B:
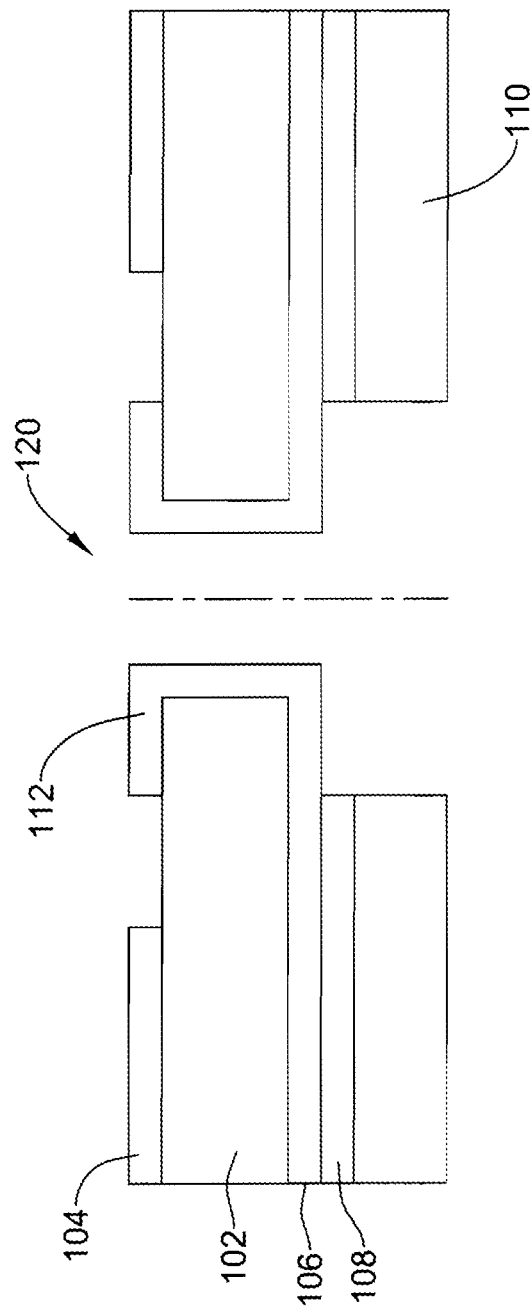
Figure 4C:
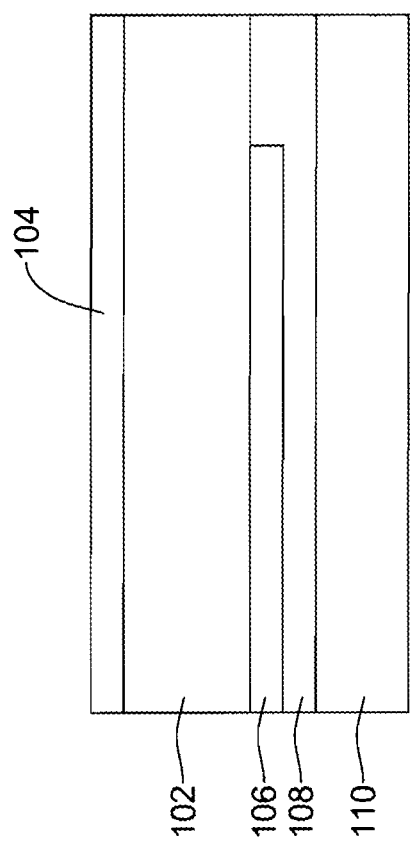

FIGS. 4A-4C show, in plan and partial sectional views, an illustrative embodiment of an EMI shield. The EMI shield is shown generally at 100, and is designed to have first and second components connected by a narrow bridge member, allowing it to fold around operational circuitry. The EMI shield 100 may be fabricated in any manner allowing for the multi-layered constructions described herein. For example, the EMI shield 100 may be manufactured as a flexible printed circuit board. In the embodiment shown, the canister for the implantable medical device includes first and second major faces, with the EMI shield 100 shaped as shown to correspond to the major face(s) of the device. In other embodiments, the EMI shield 100 may be shaped as desired. For example, conformal ICDs are shown in U.S. Pat. No. 6,647,292, having longer, curved housings; an EMI shield 100 may be shaped or formed differently for such applications. The EMI shield 100 may also be sized to cover only a desired region of the implantable medical device.

FIG. 4B highlights details around a solder pad 120 in the EMI shield 100 in FIG. 4A. The details of the illustrative EMI shield 100 that are shown in FIG. 4B away from the solder pad 120 may be consistent with the rest of the EMI shield 100 except for its edges. A first dielectric layer 102 has an outer metal layer 104 thereon. In an illustrative embodiment, the first dielectric is polyimide, though other dielectric materials may be used. An inner metal layer 106 is secured to the first dielectric layer 102. The exact construction may vary, for example, depending upon the manner of fabrication used. For example, in some embodiments, the EMI shield 100 may be constructed of separate layers that are assembled together using adhesives; in other embodiments, the EMI shield 100 may be formed by deposition processes. In the illustrative example that is shown, the metal layers 104, 106 are formed/placed on the first dielectric layer 102 in a process forming a flexible printed circuit board. If desired, the entire device may be made in such a manner, including the additional second dielectric layer 110.

In the illustrative EMI shield 100, a second dielectric layer 110 is also provided inside of the inner metal layer 106 to isolate housed operational circuitry from undesired or inadvertent contact with the inner metal layer, which may be coupled to a reference output or ground of the housed operational circuitry. While the second dielectric layer 110 may be omitted in some embodiments, it will often serve to reduce or limit cross talk and/or inadvertent shorting of sub-circuits in the device by covering some, a majority, or nearly all of the inner metal layer 106. In an illustrative embodiment, the second dielectric layer 110 is ESPANEX™ SPC-35A-25A, a laminate-ready commercially available polyimide coverlay with an adhesive 108 already provided thereon, allowing it to bond to the inner metal layer 106. Other dielectric materials may be used. The metal layers 104, 106 may be formed of any suitable conductive metal, such as silver, copper, etc., and may be selected in view of various factors such as durability, cost, resistance to corrosion, ease of manufacture, bonding or handling, and biocompatibility, for example.

FIG. 4B also shows that at the solder pad 120, the outer metal layer 104 may be pulled back such that it is separated from the portion 112 of the inner metal layer 106 that is provided to allow secure soldering. A suitable connection, such as a conductive wire, can be soldered from the operational circuitry to the solder pad 120, allowing the inner metal layer 106 to be grounded. The exposed portion 112 of the inner metal layer that extends across the first dielectric layer 102 can be covered, after soldering, with an additional dielectric patch before placing a canister thereover.

FIG. 4C illustrates a perimeter portion of the EMI shield 100. In the illustrative embodiment, the outer metal layer 104 extends virtually to the edge of the perimeter portion, while the inner metal layer 106 ends a distance away from the edge, defining a pull-back region along the perimeter. In illustrative embodiments, the pull-back region may have a width of from about 1 mil to about 100 mils, for example. By pulling the inner metal layer 106 back from the edge, the likelihood of nonlinearities (such as corona discharges) is reduced, at least at the edge of the EMI shield.

The dielectric layers 102, 110 may have thicknesses in the range of about 1-10 mils, although this may vary. In an illustrative embodiment further discussed below, the dielectric layers 102, 110 are about 2 mils thick, and the inner metal layer 106 is pulled back about 60 mils from the edge of the EMI shield 100.

Figure 4D:
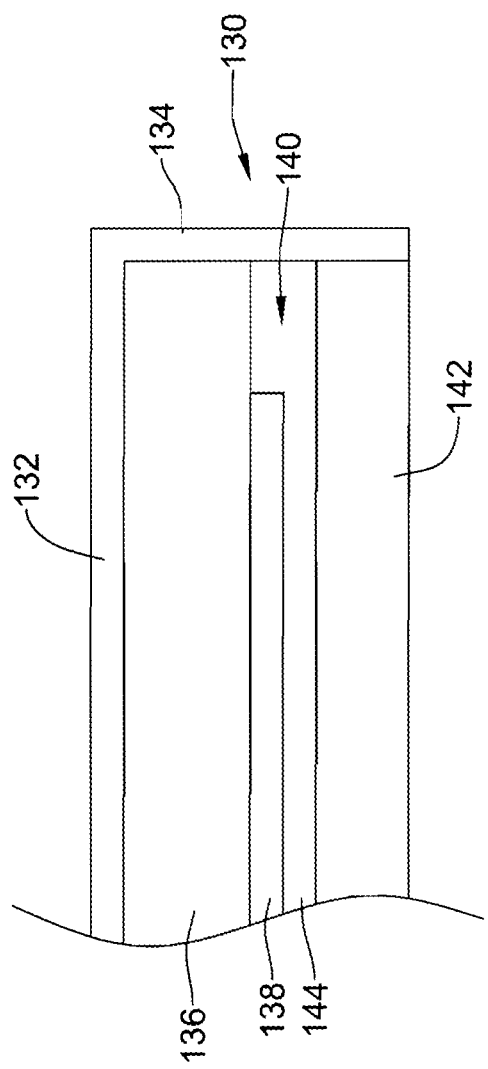
FIG. 4D is a partial sectional view showing an alternative construction to that shown in FIG. 4C.

FIG. 4D is a partial sectional view showing an alternative construction to that shown in FIG. 4C. In the alternative construction, an EMI shield 130 includes an outer metal layer 132 having a portion that extends around the edge of the shield, as shown at 134. Again, the inner metal layer 138 is shown ending a distance away from the edge of the perimeter of the EMI shield 130. An adhesive 144 may be used to secure the inner metal layer 138 to a second dielectric layer 142, as well as to join the first dielectric layer 136 and second dielectric layer 142 in the pull-back region 140 between the perimeter of the EMI shield 130 and the outer perimeter of the inner metal layer 138 and the edge of the perimeter of the EMI shield 130. The dielectric layers 136, 142 may have differing thicknesses, as shown.

Referring briefly back to FIG. 3, it can be seen that the edge of the EMI shield may be exposed to the interior of the canister. In the embodiment of FIG. 4D, extending the outer metal layer 132 to wrap around the edge of the perimeter of the EMI shield 130, as shown at 134, provides an additional "touch-point" for touching the outer metal layer 132 to the canister (see FIG. 3). Further, the "air gap", which is further explained below, can be eliminated along this portion of the device. As further illustrated in FIG. 11, the provision of one or more touch points between the conductive outer metal layer 132 and the canister may aid in reducing corona discharge.

Figure 5:
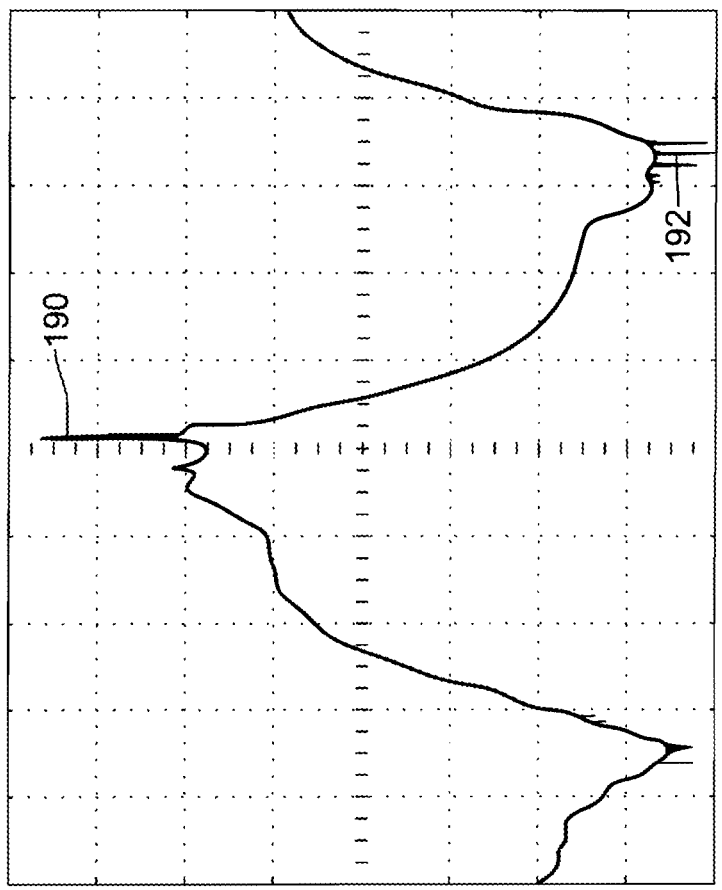
FIG. 5 shows an oscilloscope output illustrating corona discharges when the design of FIGS. 2A-2B is used as an EMI shield during a simulated high voltage signal application.

FIG. 5 shows an oscilloscope output illustrating corona discharge when the EMI shield of FIGS. 2A-2B is used as a shield during a simulated high voltage pulse. As explained above, the testing methods used applied a 60-Hz sinusoidal signal. A problem with the waveform in FIG. 5 is the nonlinearities that are visible at 190, 192. These spikes 190, 192 are caused by corona discharges that occur across the air gaps between the outer dielectric layer 64 (FIG. 2B) of the EMI shield and the interior of the canister. These corona discharges can become large enough to be visualized as sparks along the outside edge of the EMI shield under the right circumstances.

The corona discharge may be the cause of at least some system resets, as well as other electronics problems that occur during testing of ICDs using the shield shown in FIGS. 2A-2B. To provide a rough measure of the frequency and amplitude of such spikes, the above described testing setup and procedure was used. Prior to applying a signal, the capacitance of the testing structure was determined using a commercially available device for testing capacitance. Using a formula relating RMS current to frequency, voltage and capacitance ($I=2\pi f*C*V$), an expected current was determined. Actual current was then monitored during testing. Comparing the actual current to the expected current provides an estimate of the effectiveness of the EMI shield in preventing corona discharges.

The results for the EMI shield of FIGS. 2A-2B showed individual corona discharges of up to 1.5 mA, and a difference between average and expected RMS current of about 0.6 mA rms at 1000 Vrms, meaning that the average current about tripled the expected current. The oscilloscope output shown in FIG. 5 clearly shows large spikes resulting from corona discharges occurring at and near the signal peaks. In testing, nonlinearities could be detected at voltages as low as 300 Vrms.

Figure 6A:
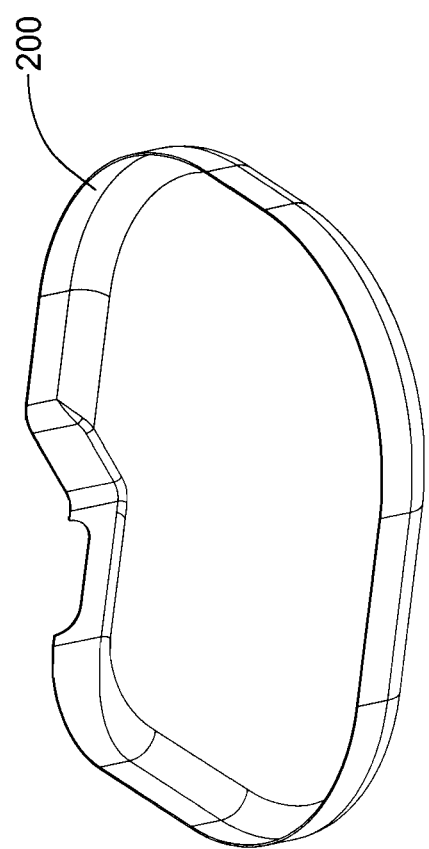
FIG. 6A illustrates, in perspective view, a PEEK insulating liner.
Figure 6B:
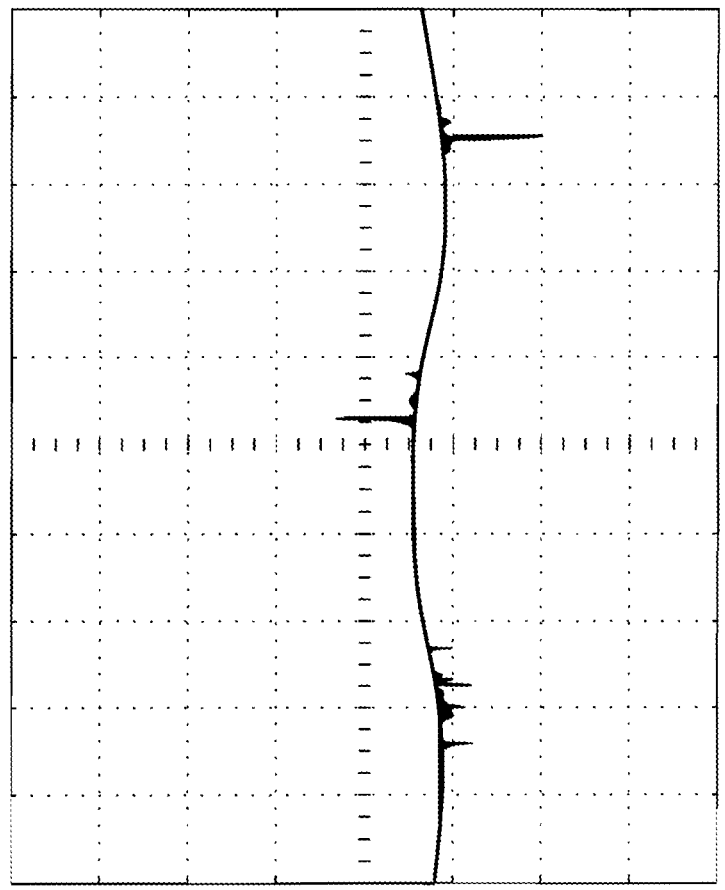
FIG. 6B shows an oscilloscope output illustrating corona discharges when the design of FIGS. 2A-2B is used with the insulating liner of FIG. 6A as an EMI shield during a simulated high voltage signal application.

FIG. 6A illustrates, in a perspective view, a PEEK insulating liner 200. The PEEK liner 200 is about 4 mils thick, and is shaped to be placed between an EMI shield as shown in FIGS. 2A-2B and a canister for an implantable medical device. FIG. 6B shows the oscilloscope output for the instantaneous current using the PEEK liner 200 in addition to an EMI shield as in FIGS. 2A-2B. The scale is the same in FIG. 6B as in FIG. 5. The average current was greatly reduced by the addition of more insulation. However, current spikes from corona discharge are also clearly visible. As measured at 1000 Vrms applied signal, the difference between average and expected current is in the range of 0.023 mA rms, and corona discharges of up to 0.5 mA were identified. The increase in average current was in the range of 20% relative to expected current.

Additional modifications to the original shield were tried as well. These included doubling the thickness of the polyimide dielectric layers to 2 mils, and pulling the metallic layer back 60 mils from the edge, rather than the original 10 mils. These tests showed a difference of 0.095 mA rms between average and expected current at 1000 Vrms, nearly doubling the current, and individual corona discharges as large as 0.5 mA. Extra insulation on the face and edges was an improvement, but corona was still prevalent.

Figure 7A:
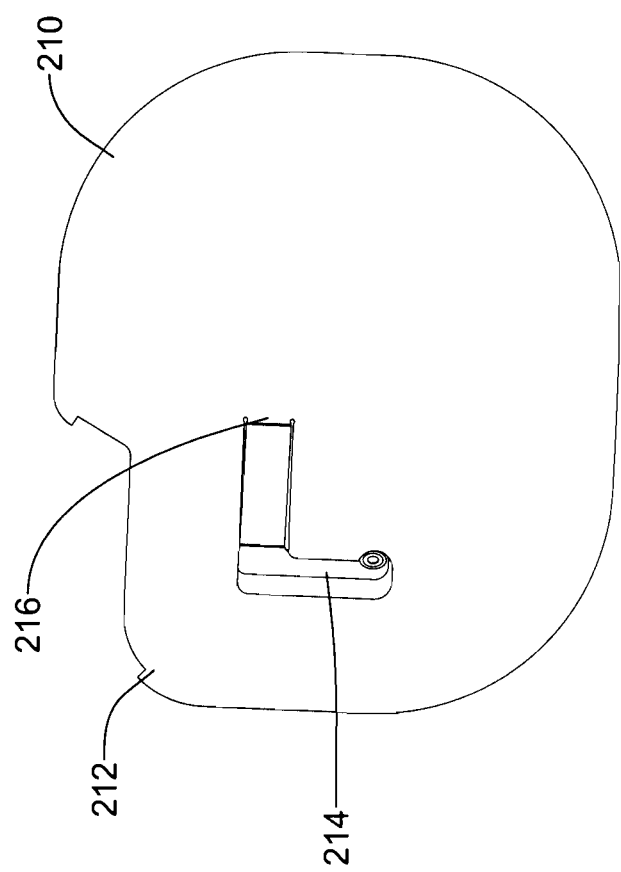
FIG. 7A illustrates, in perspective view, an EMI shield having varnish applied along the edges thereof.
Figure 7B:
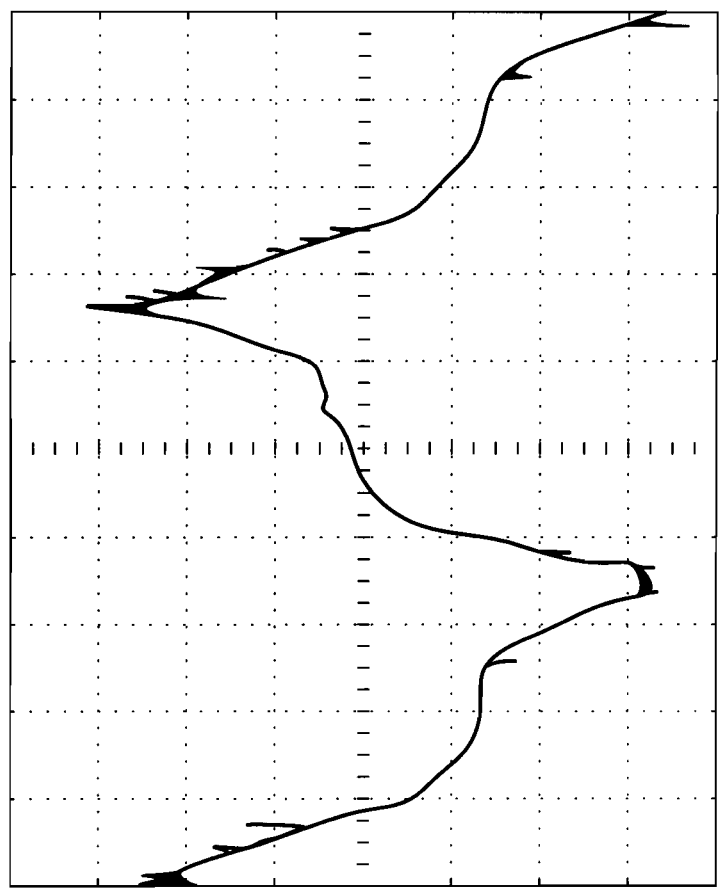
FIG. 7B shows an oscilloscope output illustrating corona discharges when the varnished EMI shield of FIG. 7A is used as an EMI shield during a simulated high voltage signal application.

FIG. 7A illustrates, in perspective view, an EMI shield 210 having varnish 212 applied to the outer edges thereof, and varnish 216 applied around solder pad 214. The applied varnish 212, 216 was an insulating varnish with an insulating strength in the range of 1000 V/mil. As shown in the oscilloscope output of FIG. 7B, a strong out-of-phase current resulted at 1000 Vrms, with relatively large and frequent corona discharge for the EMI shield of FIG. 7A. A difference of 0.82 mA rms between expected and average current resulted, nearly tripling the current, with spikes as large as 0.7 mA.

Figure 8A:
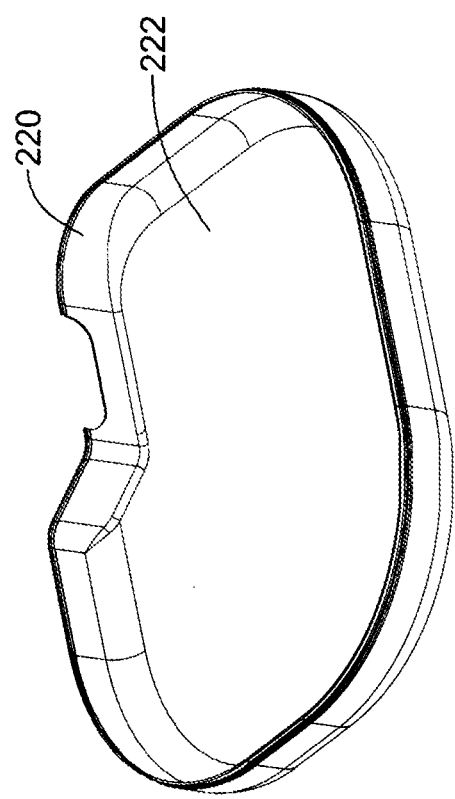
FIG. 8A illustrates, in perspective view, a varnished canister.

FIG. 8A illustrates, in perspective view, a varnished canister. The varnish 222 was applied to the entire interior of the can 220. Again, the applied varnish was an insulating varnish with an insulating strength in the range of about 1000 V/mil. As shown in FIG. 8B, the varnished canister again provided a strong out-of-phase component, with corona discharge still occurring, although with less amplitude and frequency. In testing, at 1000 Vrms applied signal, the difference between average and expected current was about 0.39 mA rms, nearly tripling the expected current, with spikes as large as 0.3 mA. Full insulation on the can reduced corona, but did not eliminate it.

Figure 9:
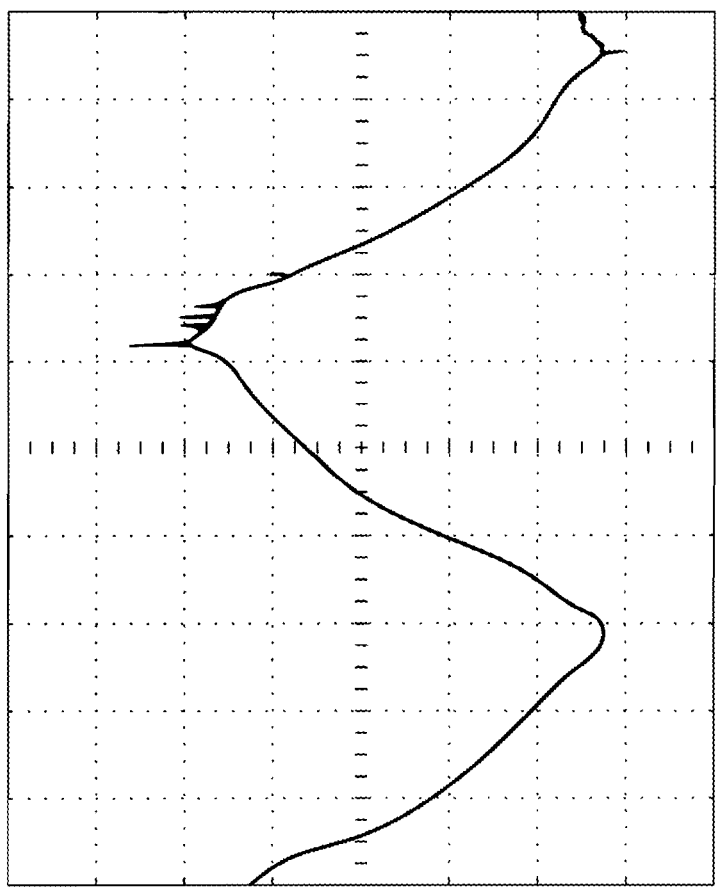
FIG. 9 shows an oscilloscope output illustrating corona discharges when the design of FIGS. 2A-2B is used as an EMI shield while adhered to a canister during a simulated high voltage signal application.

FIG. 9 shows an oscilloscope output illustrating corona discharge when the EMI shield of FIGS. 2A-2B is used as a shield while adhered to a canister during a simulated high voltage pulse. Here, adhesive was applied to the interior of a canister, and the EMI shield was placed therein, with the aim of reducing and/or eliminating air gaps across which corona discharge formed in the above tests. At 1000 Vrms, the difference between expected and average current was about 0.186 mA rms, representing a change of around 20%, with individual discharge spikes as large as 0.4 mA. Corona discharges were still present with adhesive, but they were greatly reduced simply by bonding the shield to the can. Since this adhesive only covered approximately 75% of the shield surface area, it was not fully effective.

Figure 10:
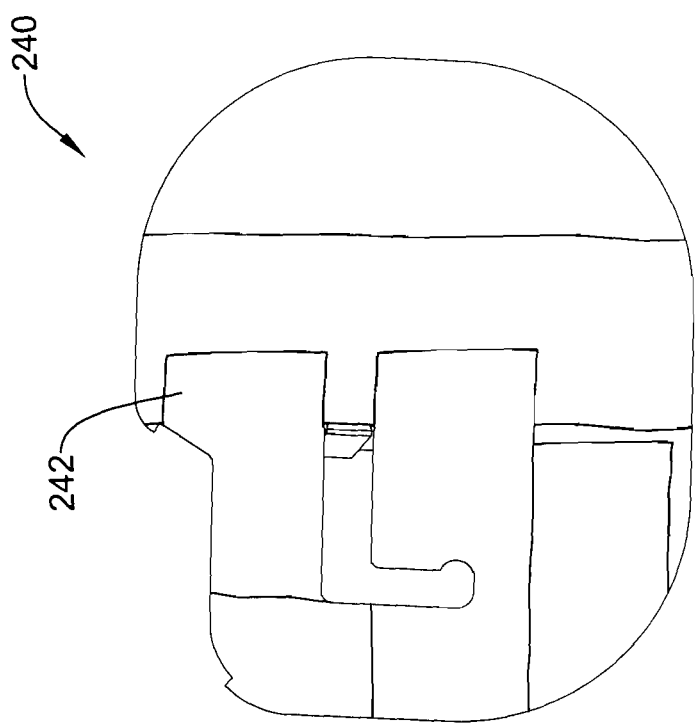
FIG. 10 is a perspective view showing an illustrative embodiment including an EMI shield having metallized tape applied to the outside thereof.

FIG. 10 is a perspective view showing an illustrative embodiment of the present invention including an EMI shield 240 having metal tape 242 applied to the outside thereof. The aim was to eliminate air gaps having large voltages across them. The metallized tape 242 would conduct electricity from the can to itself, eliminating voltage across air gaps between the EMI shield 240 and the outer can. Because it was adhered first to the EMI shield 240, the metallized tape 242 would not introduce additional air gaps between its metal and the metal layer of the EMI shield 240, placing the voltage across only the dielectric. The dielectric would now include the polyimide layer and any adhesives between the EMI shield 240 metal layer and the metal layer on the metal tape 242.

Figure 11:
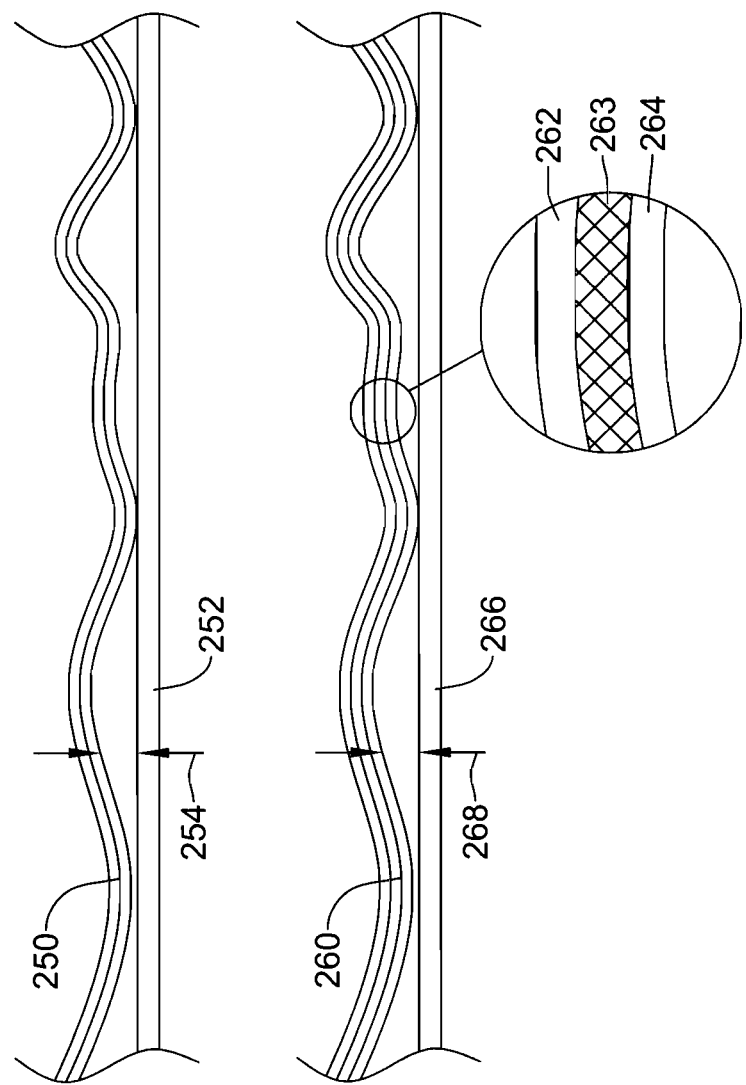
FIG. 11 illustrates, for comparison, a sectional view of the shield of FIGS. 2A-2B in contact with a canister in contrast to a section view of the shield of FIG. 10 in contact with a canister.

FIG. 11 provides an exaggerated illustration comparing a sectional view of a shield 250 as in FIGS. 2A-2B in contact with a canister 252 to a sectional view of a shield 260 as in FIG. 10 in contact with a canister 266. At 254, an air gap is seen between the shield 250 (which includes exaggerated curvature) and the canister 252. Supposing an applied 1400-volt pulse, the potential across the air gap would be about 1400 volts, possibly enough to induce breakdown such as corona discharge, depending upon humidity, temperature, and the size of the gap. The surface of the EMI shield 250 formed by the dielectric will have a voltage gradient due to its high resistivity. The contact between the EMI shield 250 and the canister 252 does not eliminate the voltage across air gaps.

The other EMI shield 260 includes an inner metal layer 262, a dielectric 263, and an outer metal layer 264. As shown at 268, air gaps may also occur with the EMI shield 260. However, the conductivity of the outer metal layer 264 eliminates the voltage potential across the air gap. The voltage gradient across the surface of the metal layer will be minimal compared to that of the dielectric surface on the other EMI shield 250. The "touch points" that surround the air gap at 268 short the voltage across the air gap, preventing corona discharge.

Figure 12:
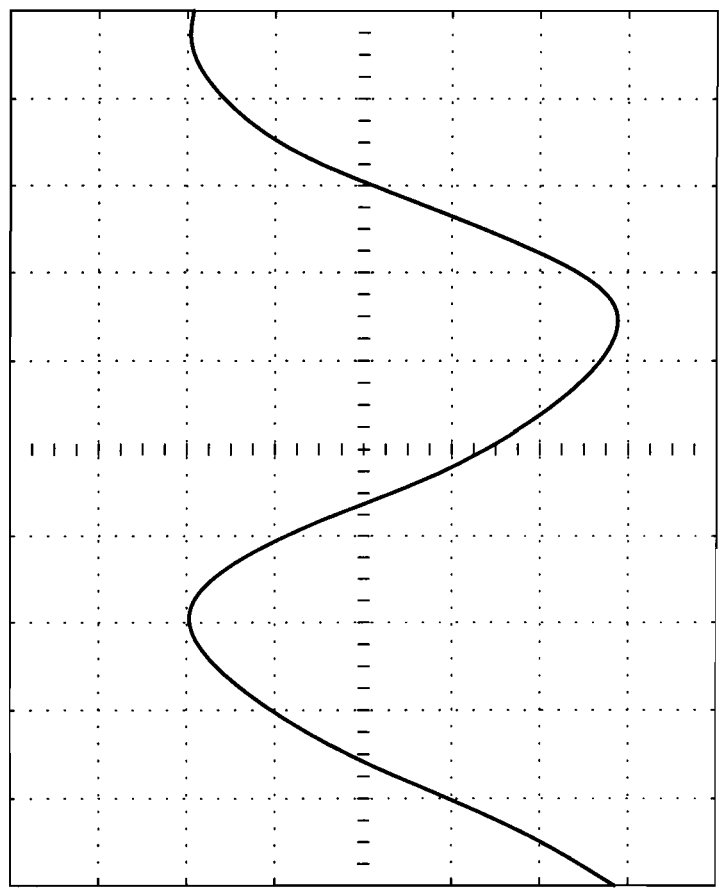
FIG. 12 shows an oscilloscope output illustrating linear response when the EMI shield of FIG. 10 is used as a shield during a simulated high voltage pulse.

FIG. 12 shows an oscilloscope output illustrating linear response when the EMI shield of FIG. 10 is used with high voltage applied. The results in FIG. 12 show substantial elimination of the corona discharge. The difference between average and expected current at 1000 Vrms was about 0.07 mA rms. Current spikes of individual discharges were not detectable on the same scale as the other designs; changing the scale of the oscilloscope showed infrequent current spikes of less than 0.06 mA. This prototype EMI shield used metallized tape, and was rather rough in its execution (i.e., there may have been gaps between tape pieces, flaws in the insulation due to handling, and the tape may not have bonded perfectly, leaving internal air gaps, etc.). It was expected that further refinement, for example, construction of the EMI shield as shown in FIGS. 4A-4C, would improve performance.

Another prototype having the metallized tape was prepared, this time using an EMI shield having double the insulation (2 mils of polyimide instead of 1 mil) and including a metal layer pulled back 60 mils, rather than 10 mils, from the edges. This improved on the performance, and reduced the difference between average and expected current at 1000 Vrms to 0.016 mA rms. Current spikes were again infrequent, and this time had amplitudes of less than 0.03 mA. Compared to the originally tested shield of FIGS. 2A-2B, the frequency and amplitude of corona discharges was greatly reduced. At 1000 Vrms, the average current was reduced from 0.6 mA rms to 0.016 mA rms (⅟₃₈th) and maximum corona amplitudes reduced from 1.5 mA to 0.03 mA (⅟₅₀th).

Figure 13A:
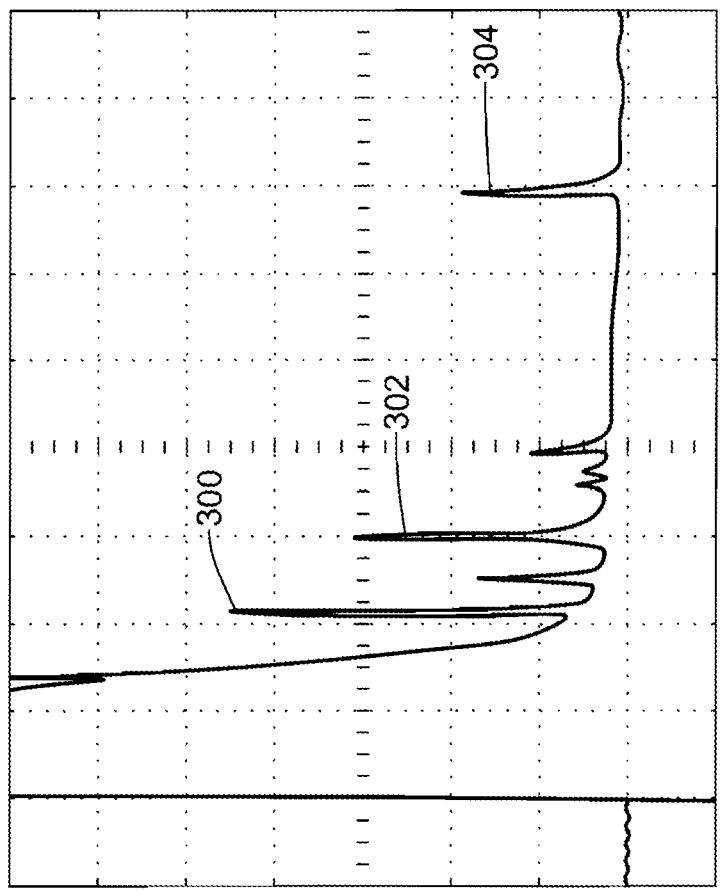
FIGS. 13A-13B and 14A-14B show oscilloscope outputs comparing performance of an EMI shield as in FIGS. 2A-2B to that of an EMI shield as shown in FIG. 10 during delivery of simulated high voltage pulses.
Figure 13B:
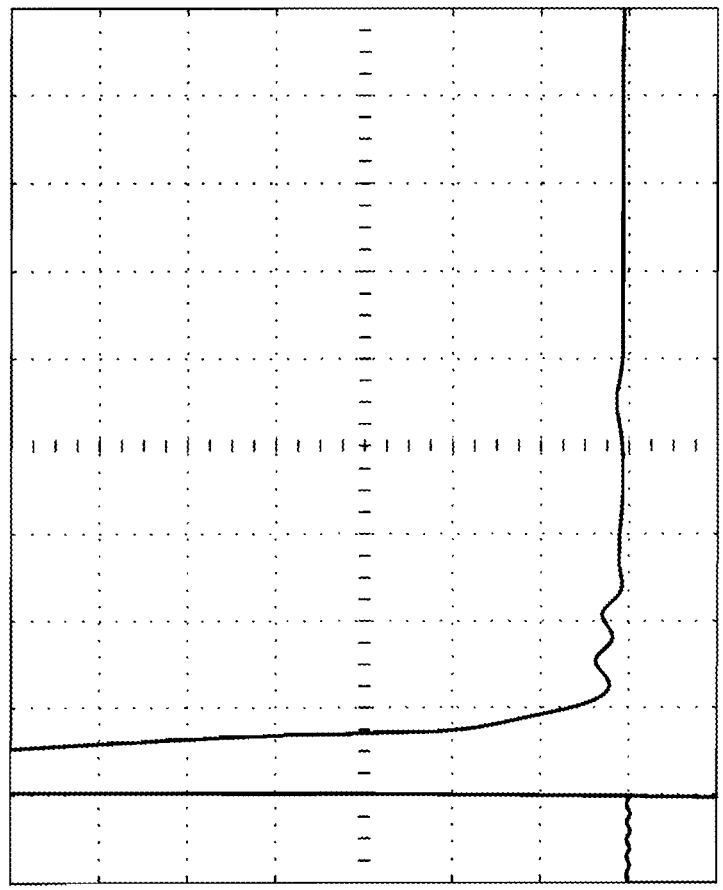
Figure 14A:
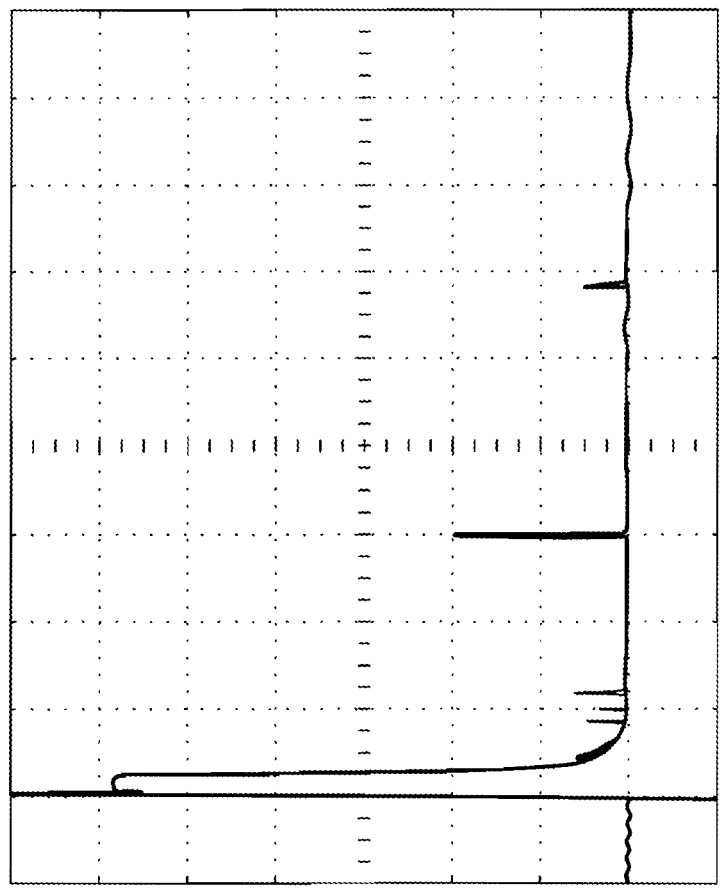
Figure 14B:
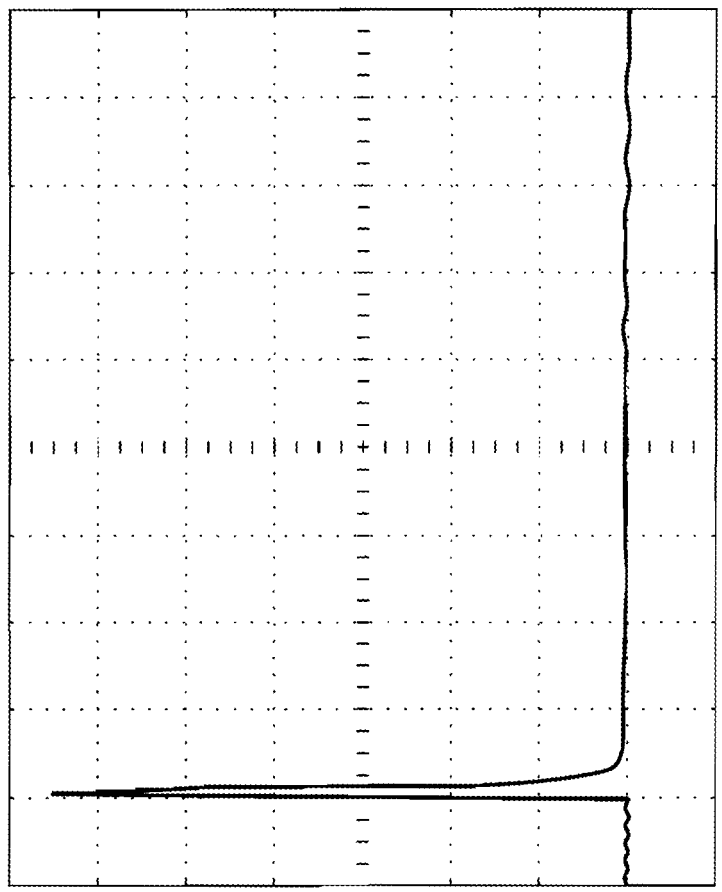

FIGS. 13A-13B and 14A-14B show oscilloscope outputs comparing the performance of a shield as in FIGS. 2A-2B to that of a shield having doubled insulation (2 mils of polyimide), with an inner metal layer pulled back 60 mils (as compared to 10 mils), and including metallized tape on the outside. This time, high voltage pulses were tested. FIG. 13A shows the oscilloscope for a 1350-volt shock waveform using the EMI shield of FIGS. 2A-2B. Large spikes are clearly shown at 300, 302, and even at 304, with a peak amplitude of the corona discharges being in the range of 80 mA. Meanwhile, as shown in FIG. 13B, which uses the same scale as FIG. 13A, no corona discharge spikes are seen with the EMI shield having doubled insulation, a larger pull-back region, and metal tape. A broader scale is shown in FIGS. 14A-14B, further highlighting the differences in performance.

Further prototypes were prepared, this time in accordance with the designs of FIGS. 4A-4C. Six EMI shields (three of each of the two types) were tested. The testing involved using an external power supply for the system, but the internal control circuitry for an implantable cardioverter defibrillator was powered and active during shock delivery, in order to observe whether the control system reset during the shock delivery. Telemetry was also performed to assess the effect of the EMI shields on the rate of framing errors that occurred during telemetry communications.

Figure 15A:
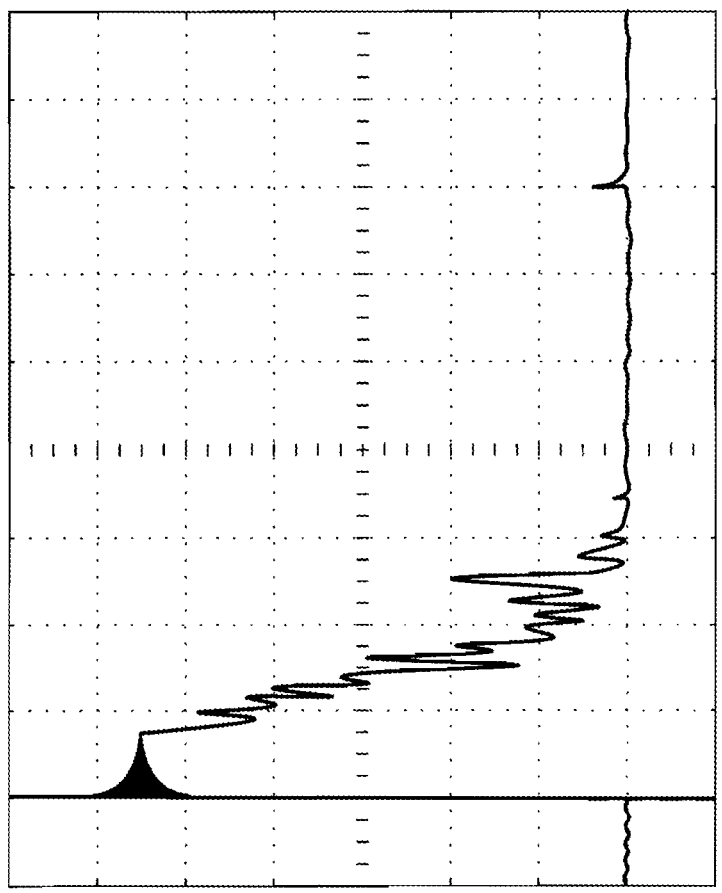
FIGS. 15A-15B show oscilloscope outputs comparing performance of an EMI shield as shown in FIGS. 2A-2B to that of an EMI shield as shown in FIGS. 4A-4C.

During delivery of shock waveforms near 1380 Volts, control circuitry in devices having shields similar to those shown in FIGS. 2A-2B reset during shock delivery 62/80, 13/53, and 14/24 times for the three different prepared shields. FIG. 15A shows the oscilloscope output for one of the shocks delivered with the shield of FIGS. 2A-2B, and includes significant apparent corona discharge effects. In contrast, control circuitry in devices having the shields as shown in FIGS. 4A-4C, using amplitudes in the same range of 1380 volts, did not reset a single time during 231 tests (0/80, 0/80 and 0/71 for the three prepared EMI shields). Testing used the same three sets of circuitry for both series of tests, in order to show that the shields themselves, rather than the circuitry, caused the difference in performance.

Figure 15B:
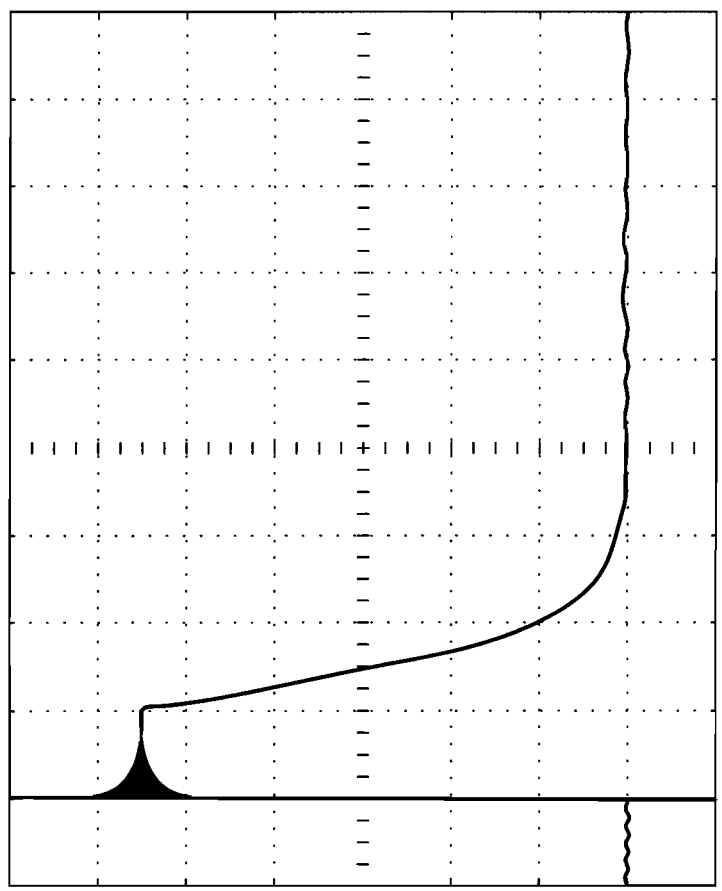

FIG. 15B shows the oscilloscope output for one of the shocks delivered with the shield of FIGS. 4A-4C in place, and does not include the corona discharge effects seen with the other shield. During testing, there was one device which failed. However, this was determined to be caused by an error during assembly that caused damage to a system component, and was not related to the efficacy of the EMI shield. It was found that the sets of shields performed comparably with respect to framing errors and noise.

With respect to measurement of expected and average current, the metal tape prototype testing was further confirmed. For the devices having the EMI shields as shown in FIGS. 2A-2B, corona discharge was apparent in response to applied 60-Hz sinusoid at 1000 Vrms and 2000 Vrms, with spikes as large as 2 mA, and with corona discharge appearing at applied voltages exceeding 240 Vrms. Spiking was not detected for the EMI shields as shown in FIGS. 4A-4C in response to an applied 60-Hz sinusoid at 1000 Vrms, with testing including observation at scales that would show spikes as small as 0.01 mA. At 2000 Vrms, the EMI shields as shown in FIGS. 4A-4C allowed current spikes in the range of 0.03 mA in amplitude, with these relatively small current spikes being first observed at around 1050 Vrms.

Figure 16A:
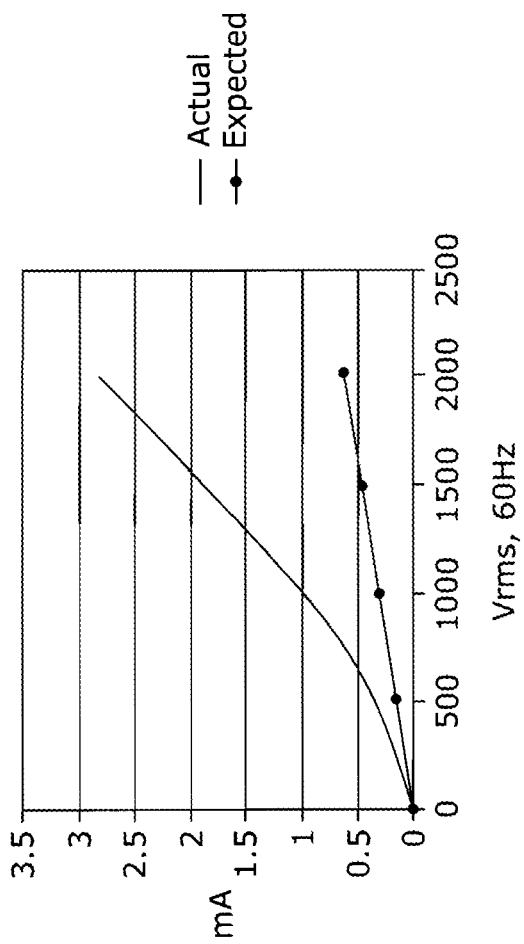
FIGS. 16A-16B are graphs showing expected versus average detected currents for tested EMI shields.
Figure 16B:
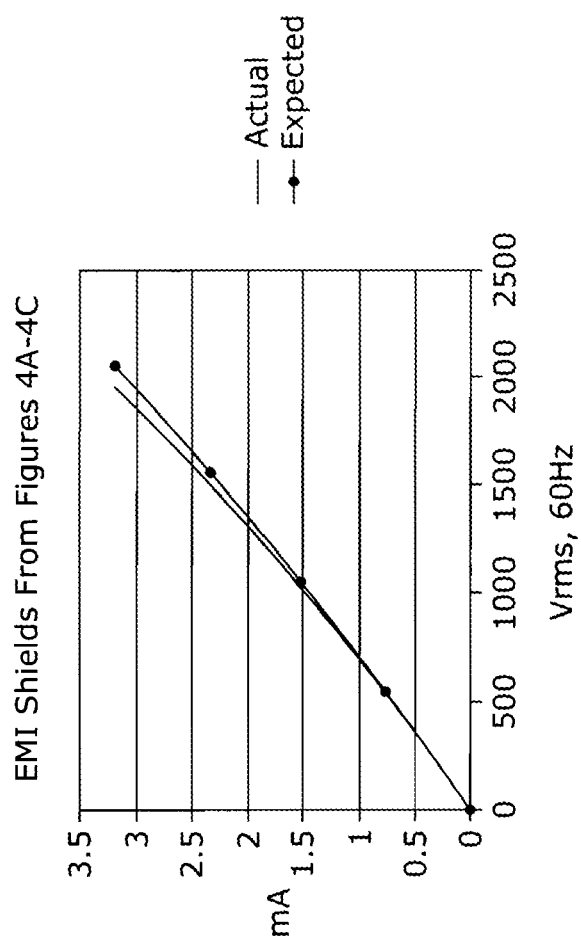

FIG. 16A shows results for expected versus average current with the EMI shields as shown in FIGS. 2A-2B for three tested EMI shields. Significant deviation from the expected current occurred for these EMI shields. FIG. 16B shows results for EMI shields as shown in FIGS. 4A-4C on the same scale used in FIG. 16A. In contrast to the other EMI shields, minimal deviation occurs, indicating very limited corona discharge.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of treating a patient comprising implanting an implantable cardiac stimulus device (ICSD), wherein the ICSD comprises:
   operational circuitry adapted to sense cardiac activity and provide cardiac stimulus output;
   a canister made of a conductive metal and forming a housing for containing the operational circuitry, the housing having first and second major faces; and
   an EMI shield comprising an outer metal layer and an inner metal layer with a dielectric therebetween;
   wherein the EMI shield separates the operational circuitry from one of the major faces of the housing such that the outer metal layer is in electrically conductive contact with the canister.

2. The method of claim 1, wherein the outer metal layer of the EMI shield is electrically isolated from the inner metal layer of the EMI shield.

3. The method of claim 1, wherein the inner metal layer of the EMI shield of the ICSD is electrically connected to a reference ground of the operational circuitry.

4. The method of claim 1 wherein:
   the EMI shield of the ICSD includes an outer perimeter;
   the inner metal layer of the EMI shield covers a major portion of a first side of the EMI shield; and
   the inner metal layer does not extend to a pull-back region adjacent the outer perimeter.

5. The method of claim 4, wherein the pull-back region has a width of about 60 mils.

6. The method of claim 4, wherein the outer metal layer extends around the dielectric at the perimeter.

7. The method of claim 1, wherein the EMI shield of the ICSD further includes an inner dielectric layer covering a major portion of the inner metal layer and substantially isolating the operational circuitry from contact with the inner metal layer.

8. The method of claim 1, wherein:
   the ICSD further includes a first electrode disposed on the canister;
   the ICSD further comprises a lead assembly coupled to the operational circuitry via a header provided on the canister, the lead assembly including at least a second electrode; and
   the operational circuitry includes high-voltage capacitors and a battery system and is adapted to deliver a stimulus output in the range of more than 50 V in amplitude using an electrode system including the first and second electrodes.

9. The method of claim 1, wherein:
   the ICSD includes a first electrode disposed on the canister;
   the ICSD further comprises a lead assembly coupled to the operational circuitry via a header provided on the canister, the lead assembly including at least a second electrode; and
   the operational circuitry includes high-voltage capacitors and a battery system and is adapted to deliver a stimulus output sufficient to achieve cardioversion/defibrillation of a patient into whom the ICSD can be implanted.

10. The method of claim 1 further comprising using a programmer following implantation of the implantable device to activate the implantable device.

11. The method of claim 1 further comprising using a programmer following implantation of the implantable device to direct operation of the implantable device.

12. The method of claim 1 further comprising using a programmer following implantation of the implantable device to observe a diagnostic or operational test of the implantable device.

13. The method of claim 1 further comprising using a programmer after implantation of the implantable device to non-invasively determine the status and history of the implantable device.

* * * * *